(12) United States Patent
Chen et al.

(10) Patent No.: US 10,099,050 B2
(45) Date of Patent: Oct. 16, 2018

(54) INTERVENTIONAL MEDICAL DEVICES, DEVICE SYSTEMS, AND FIXATION COMPONENTS THEREOF

(71) Applicant: Medtronic, Inc., Minneapolis, MN (US)

(72) Inventors: Xin Chen, Circle Pines, MN (US); Michael D. Eggen, Chisago City, MN (US); Vladimir Grubac, Brooklyn Park, MN (US); Brian P. Colin, Shakopee, MN (US); Wei Gan, Woodbury, MN (US); Thomas A. Anderson, New Hope, MN (US); Kathryn Hilpisch, Cottage Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 86 days.

(21) Appl. No.: 15/410,161

(22) Filed: Jan. 19, 2017

(65) Prior Publication Data

US 2017/0209689 A1 Jul. 27, 2017

Related U.S. Application Data

(60) Provisional application No. 62/281,403, filed on Jan. 21, 2016.

(51) Int. Cl.
*A61N 1/00* (2006.01)
*A61N 1/05* (2006.01)
(Continued)

(52) U.S. Cl.
CPC ........... *A61N 1/0573* (2013.01); *A61N 1/362* (2013.01); *A61N 1/3756* (2013.01); *A61N 1/37205* (2013.01); *A61N 2001/058* (2013.01)

(58) Field of Classification Search
CPC .... A61N 1/057; A61N 1/0573; A61N 1/3756; A61N 1/362
(Continued)

(56) References Cited

U.S. PATENT DOCUMENTS 3,814,104 A 6/1974 Irnich et al.
4,103,690 A 8/1978 Harris
(Continued)

OTHER PUBLICATIONS http://www.mana-tech.com/factsheets/HomerMammalok.pdf.
(Continued)

*Primary Examiner* — Amanda Hulbert
*Assistant Examiner* — Philip C Edwards

(57) ABSTRACT

A fixation mechanism of an implantable medical device is formed by a plurality of tines fixedly mounted around a perimeter of a distal end of the device. Each tine may be said to include a first segment fixedly attached to the device, a second segment extending from the first segment, and a third segment, to which the second segment extends. When the device is loaded in a lumen of a delivery tool and a rounded free distal end of each tine engages a sidewall that defines the lumen, to hold the tines in a spring-loaded condition, the first segment of each tine, which has a spring-biased preformed curvature, becomes relatively straightened, and the third segment of each tine, which is terminated by the free distal end, extends away from the axis of the device at an acute angle in a range from about 45 degrees to about 75 degrees.

31 Claims, 12 Drawing Sheets

(51) Int. Cl.
*A61N 1/362* (2006.01)
*A61N 1/375* (2006.01)
*A61N 1/372* (2006.01)

(58) Field of Classification Search
USPC .......................................................... 607/126
See application file for complete search history.

(56) References Cited

U.S. PATENT DOCUMENTS

| | | | |
|---|---|---|---|
| 6,055,457 | A | 4/2000 | Bonner |
| 6,738,672 | B2 | 5/2004 | Schulman et al. |
| 6,823,217 | B2 | 11/2004 | Rutten et al. |
| 7,082,336 | B2 | 7/2006 | Ransbury et al. |
| 7,130,700 | B2 | 10/2006 | Gardeski et al. |
| 7,331,922 | B2 | 2/2008 | Mohl |
| 7,647,109 | B2 | 1/2010 | Hastings et al. |
| 7,949,395 | B2 | 5/2011 | Kuzma |
| 8,012,127 | B2 | 9/2011 | Lieberman et al. |
| 8,032,219 | B2 | 10/2011 | Neumann et al. |
| 8,262,672 | B2 | 9/2012 | Neidert et al. |
| 8,478,431 | B2 | 7/2013 | Griswold et al. |
| 8,532,790 | B2 | 9/2013 | Griswold |
| 8,615,310 | B2 | 12/2013 | Khairkhahan et al. |
| 8,634,912 | B2 | 1/2014 | Bornzin et al. |
| 8,670,842 | B1 | 3/2014 | Bornzin et al. |
| 8,755,909 | B2 | 6/2014 | Sommer et al. |
| 9,119,959 | B2 | 9/2015 | Rys et al. |
| 9,155,882 | B2 | 10/2015 | Grubac et al. |
| 9,414,857 | B2 | 8/2016 | Wood et al. |
| 9,446,248 | B2 | 9/2016 | Sheldon et al. |
| 9,526,891 | B2 | 12/2016 | Eggen et al. |
| 9,539,423 | B2 | 1/2017 | Bonner et al. |
| 2002/0095203 | A1 | 7/2002 | Thompson et al. |
| 2004/0147973 | A1 | 7/2004 | Hauser |
| 2006/0247753 | A1 | 11/2006 | Wenger et al. |
| 2009/0082828 | A1 | 3/2009 | Ostroff |
| 2011/0251661 | A1 | 10/2011 | Fifer et al. |
| 2011/0270340 | A1 | 11/2011 | Pellegini et al. |
| 2012/0172690 | A1 | 7/2012 | Anderson et al. |
| 2012/0172892 | A1 | 7/2012 | Grubac et al. |
| 2013/0110127 | A1 | 5/2013 | Bornzin et al. |
| 2013/0116738 | A1 | 5/2013 | Samade et al. |
| 2013/0253345 | A1 | 9/2013 | Griswold et al. |
| 2014/0107723 | A1 | 4/2014 | Hou et al. |
| 2014/0180306 | A1 | 6/2014 | Grubac et al. |
| 2015/0039070 | A1 | 2/2015 | Kuhn et al. |
| 2015/0039071 | A1 | 2/2015 | Grubac et al. |
| 2015/0051616 | A1 | 2/2015 | Haasl et al. |
| 2015/0051682 | A1 | 2/2015 | Schmidt et al. |
| 2015/0094668 | A1 | 4/2015 | Wood |
| 2015/0352353 | A1 | 12/2015 | Rys et al. |
| 2016/0001068 | A1 | 1/2016 | Grubac et al. |
| 2016/0059002 | A1 | 3/2016 | Grubac et al. |

OTHER PUBLICATIONS

Medtronic model SELECTSURE™ 3830 manual, 2013, 20 pages.
(PCT/US2017/014352) PCT Invitation to Pay Additional Fees and, Where Applicable, Protest Fee, dated Apr. 3, 2017, 7 pages.
(PCT/US2017/014361) PCT Notification of Transmittal of the International Search Report and the Written Opinion of the International Searching Authority, dated Apr. 3, 2017, 11 pages.
(PCT/US2017/014369) PCT Notification of Transmittal of the International Search Report and the Written Opinion of the International Searching Authority, dated May 10, 2017, 13 pages.

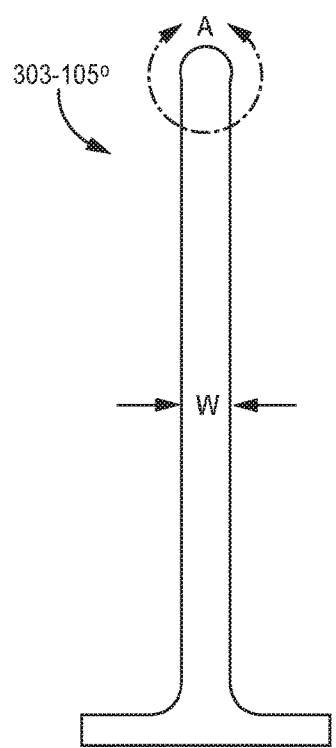 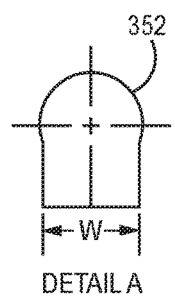 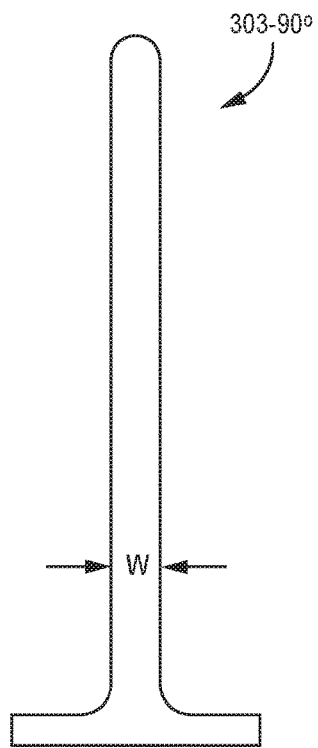
FIG. 3C        FIG. 3D

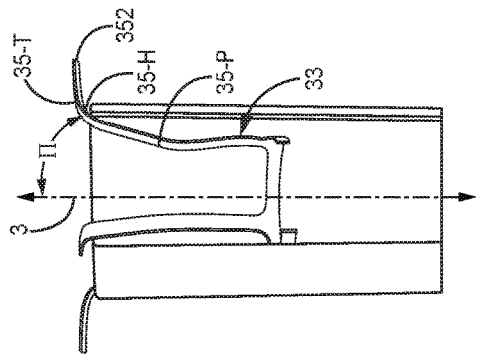
FIG. 5A
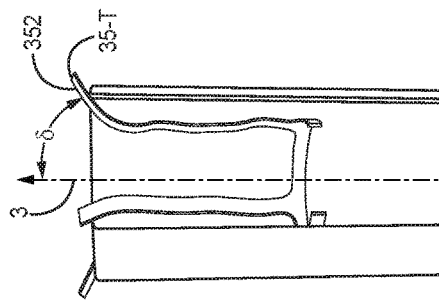
FIG. 5B
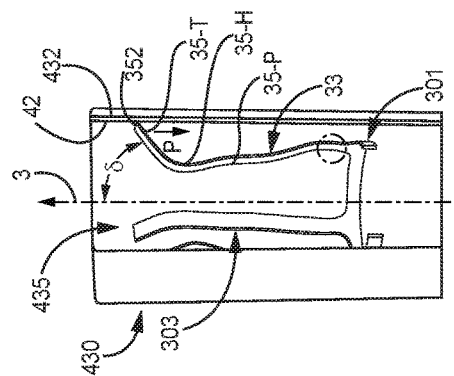
FIG. 5C
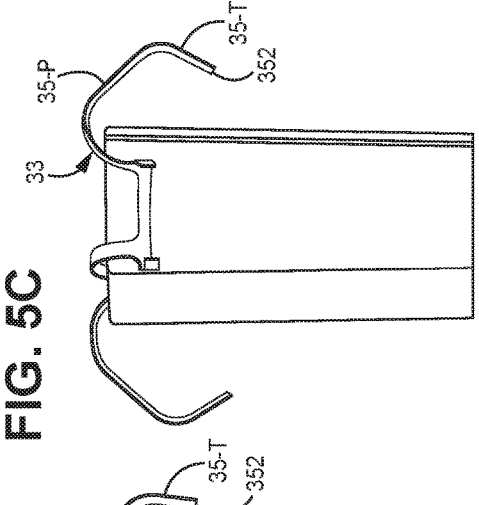
FIG. 5D
FIG. 5E
FIG. 5F
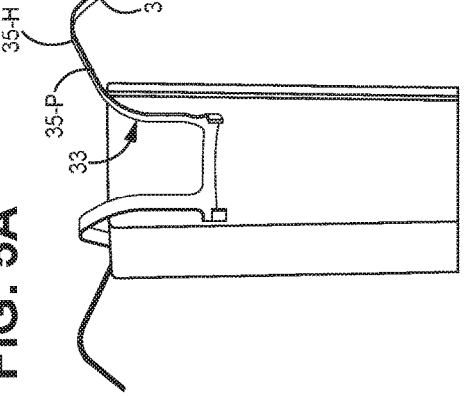

INTERVENTIONAL MEDICAL DEVICES, DEVICE SYSTEMS, AND FIXATION COMPONENTS THEREOF

CROSS-REFERENCE TO RELATED APPLICATIONS

The instant application claims priority to U.S. Provisional Patent Application having the Ser. No. 62/281,403, and the Attorney Docket No. C00012850.USP1, which was filed on Jan. 21, 2016, and which is hereby incorporated by reference in its entirety. The instant application is also related to the United States Patent Application entitled, INTERVENTIONAL MEDICAL SYSTEMS, which is filed concurrently herewith.

FIELD OF THE DISCLOSURE

The present disclosure pertains to medical device systems, and, more particularly, to relatively compact implantable medical devices thereof and associated fixation components.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical complications and/or MRI compatibility issues, which are sometimes associated with elongate lead wires and well known to those skilled in the art, have motivated the development of implantable cardiac pacing devices that are wholly contained within a relatively compact package, the entirety of which is configured for implant in close proximity to the pacing site. FIG. 1 is a schematic that shows a potential cardiac implant site for such a device within an appendage 102 of a right atrium RA. An implanting physician may employ a delivery tool 400 to deploy a relatively compact medical device to the site, for example, after maneuvering tool 400, with the device loaded therein, up through the inferior vena cava IVC and into the right atrium RA. Although some suitable configurations of a fixation component for such an implantable medical device have been disclosed, for example, in a co-pending and commonly assigned U.S. patent application having the Ser. No. 14/518,211, there is a need for new configurations of fixation components that can enhance the stability of fixation.

BRIEF SUMMARY

Embodiments of medical device systems disclosed herein include an implantable medical device and a delivery tool, wherein the device has a fixation mechanism formed by a plurality of tines fixedly mounted and spaced from one another around a perimeter of a distal end of the device, and the tool includes a tubular sidewall that defines a lumen into which the device may be loaded, the lumen having a distal opening through which the device may be deployed. In some embodiments, each tine of the device fixation mechanism includes: a first segment fixedly attached to the device and extending therefrom; a second segment extending from the first segment; and a third segment, to which the second segment extends, the third segment having a rounded free distal end spaced from the perimeter of the device housing distal end; and wherein: the first segment has a spring-biased pre-formed curvature, extending distally from the device distal end, and then sweeping laterally outward from the axis of the device and then proximally to the second segment; the second segment is pre-formed to extend proximally along a relatively straight line to the third segment, the relatively straight line of the second segment being oriented, by the spring-biased preformed curvature of the first segment, to intersect the axis of the device at an acute angle of between about 30 degrees and about 50 degrees; the third segment has a deformable pre-formed curvature that extends back toward the axis of the device such that, when the curvature of the third segment is un-deformed, the second and third segments enclose an angle in a range from about 70 degrees to about 120 degrees; and the tines are each configured such that when the device is loaded in the lumen of the tool and the rounded free distal end of the third segment of each tine engages the delivery tool sidewall to hold the tines in a spring-loaded condition, the first segment of each tine becomes relatively straightened, and the third segment of each tine extends away from the axis of the device at an acute angle in a range from about 45 degrees to about 75 degrees.

According to some embodiments, the aforementioned tines are part of a tissue penetrating fixation component that also includes a base configured to be fixedly attached to the device so that a perimeter of the component extends around an electrode of the device, and so that a longitudinal axis of the component is generally aligned along that of the device. The plurality of tines extend from the base, and each tine includes: a proximal, spring portion (corresponding to the aforementioned first segment) being fixedly attached to the base and having a spring-biased pre-formed curvature, the pre-formed curvature, in proximity to the base, extending in a first direction, generally parallel to the axis of the component, and then sweeping laterally, outward from the axis; and a distal portion (corresponding to the aforementioned second and third segments) including a proximal section, a hook section, and tip section terminated by a rounded free distal end, the proximal section extending from the proximal, spring portion and being pre-formed to extend in a second direction and along a relatively straight line to the hook section, the proximal section being oriented, by the spring-biased pre-formed curvature of the proximal, spring portion, so that the second direction is generally opposite the first direction, and the relatively straight line intersects the axis at an acute angle of between about 30 degrees and about 50 degrees, the hook section having a deformable pre-formed curvature that extends from the proximal section back toward the axis of the component, the tip section being pre-formed to extend along a relatively straight line from the hook section to the rounded free distal end, and the tip section being oriented by the pre-formed curvature of the hook section, when un-deformed, to extend toward the axis of the component, such that the tip section and the proximal section enclose an angle in a range from about 70 degrees to about 120 degrees; and wherein: when the device, having the fixation component fixedly attached thereto, is loaded within a tubular sidewall of a delivery tool, so that the rounded free distal end of each tine of the component engages an inner surface of the sidewall in proximity to a distal opening of the tool, to hold the proximal, spring portion of each tine of the component in a spring-loaded condition, each tip section of the distal portion extends away from the axis of the component at an acute angle in a range from about 45 degrees to about 75 degrees for deployment of the corresponding rounded free distal end out from the distal opening of the tool tubular sidewall; and upon deployment of the rounded free distal end of each tine, the tip section of each distal portion rotates away from the axis to approach an angle of 90 degrees, relative to the axis, in response to an initial release of the spring-loaded condition of the corresponding proximal, spring portion.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and:

FIG. 3C is a plan view of a portion of the component of FIGS. 3A-B, prior to forming, according to some embodiments;

FIG. 3D is a plan view of a portion of the component of FIGS. 3A-B, prior to forming, according to some alternate embodiments;

FIG. 5A is a schematic showing a spring loaded condition of the fixation component of the atrial portion of the device, according to some embodiments;

FIG. 5B is a schematic showing an initial release of the fixation component from the spring loading shown in FIG. 5A;

FIG. 5C is a schematic showing rotation for initial penetration of the fixation component after the initial release of FIG. 5B;

FIG. 5D is a schematic showing fixation component movement, subsequent to initial penetration;

FIG. 5E is a schematic showing fixation component movement, subsequent to penetration;

FIG. 5F is a schematic showing fixation component movement, subsequent to penetration;

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 2A:
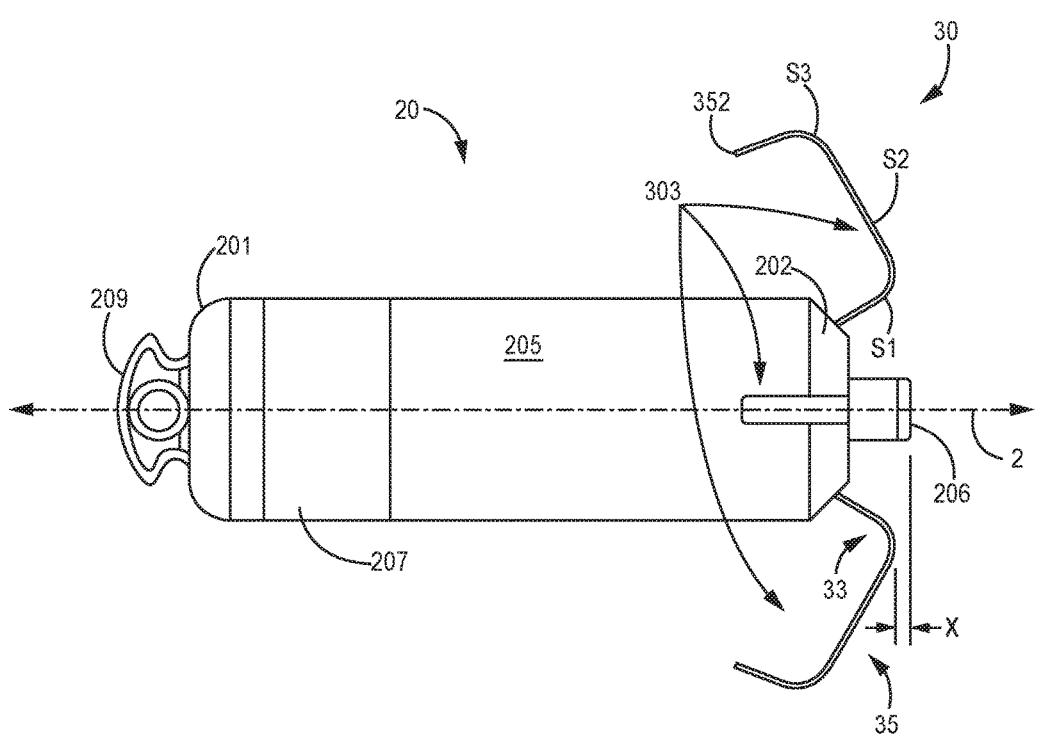
FIG. 2A is a plan view of a relatively compact implantable medical device, according to some embodiments.

FIG. 2A is a plan view of a relatively compact implantable medical device 20, according to some embodiments. FIG. 2A illustrates device 20 including a hermetically sealed housing 205, preferably formed from a biocompatible and biostable metal such as titanium, which contains a pulse generator (e.g., a power source and an electronic controller—not shown), a fixation mechanism 30, and an electrode 206, which is spaced apart from a distal end 202 of housing 205, for example, being coupled to the pulse generator by a conductor of an hermetic feedthrough assembly (not shown) that is constructed according to methods known to those skilled in the art of implantable medical devices. FIG. 2A further illustrates device 20 including a holding member 209 mounted to a proximal end 201 of housing 205, wherein holding member 209 is configured for temporarily tethering device 20 to a delivery tool, such as tool 400, according to methods known in the art.

Housing 205 may be overlaid with an insulative layer, for example, medical grade polyurethane, parylene, or silicone, and, with further reference to FIG. 2A, another electrode 207 of device 20 may be formed by removing a portion of the insulative layer to expose the metallic surface of housing 205. According to the illustrated embodiment, electrode 206 may function in conjunction with electrode 207 for bipolar pacing and sensing, when elastically deformable tines 303 of fixation mechanism 30 hold electrode 206 in intimate tissue contact at a target implant site, for example, within right atrial appendage 102 as illustrated schematically in FIG. 2B.

In FIG. 2A, one of tines 303 is shown divided into first, second, and third segments S1, S2, S3, each of which is pre-formed into, and elastically deformable from, the illustrated shape thereof. According to the illustrated embodiment, first segment S1 is fixedly attached to distal end 202 of device housing 205 and extends around a pre-formed curvature to second segment S2, which extends proximally along a relatively straight line to third segment S3. FIG. 2A illustrates third segment S3 extending around a pre-formed curvature to a free distal end 352 of tine 303.

Figure 1:
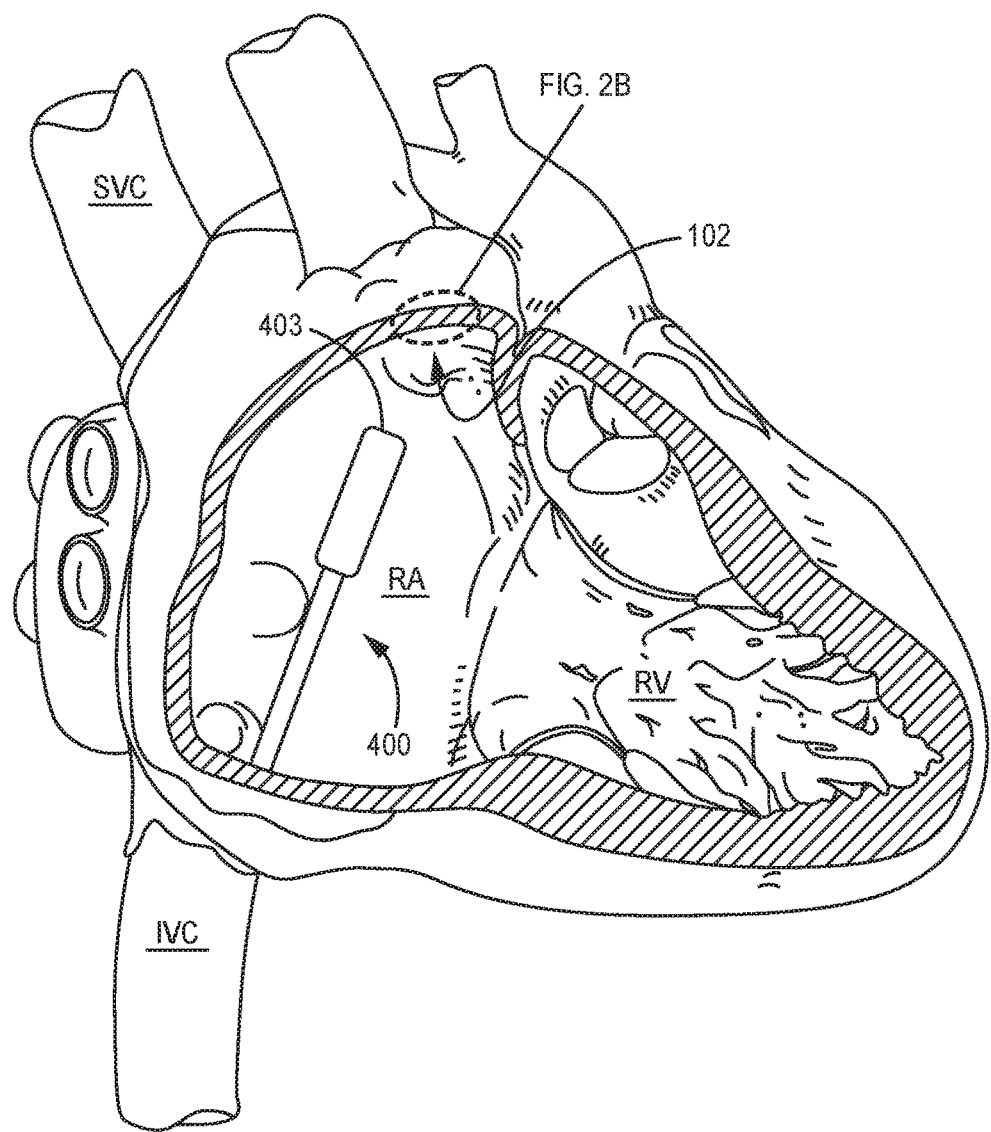
FIG. 1 is a schematic diagram showing an exemplary cardiac implant site for which embodiments of the present invention are particularly suited.
Figure 2B:
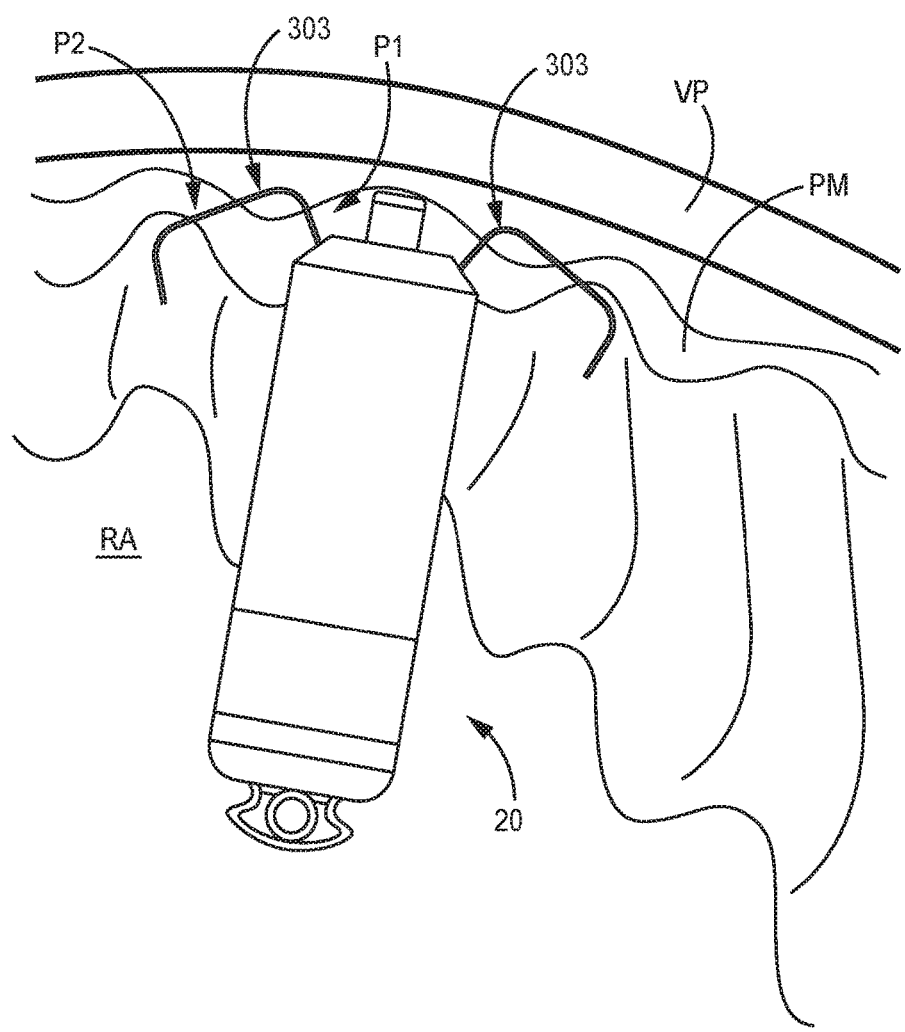
FIG. 2B is a schematic section showing the device of FIG. 2A implanted, according to some embodiments and methods.

FIG. 2B is a schematic section showing device 20 implanted in right atrium RA (FIG. 1), according to some embodiments and methods. With reference to FIG. 2B, a portion the right atrial wall, for example, in appendage 102, is shown having a laminate structure that includes an inner layer of pectinate muscle PM and an outer layer of visceral pericardium VP, which forms the epicardial surface. FIG. 2B illustrates device 20 secured at the implant site by tines 303 of fixation mechanism 30 penetrating through the layer of pectinate muscle PM without perforating through visceral pericardium VP, which could result in pericardial effusion. Tines 303 of mechanism 30, according to embodiments disclosed herein, are configured for spring-loaded release, upon deployment out through a distal opening 403 of a lumen 435 of delivery tool 400, as described below in conjunction with FIGS. 4 and 5B-C, so that tine free distal end 352 penetrates pectinate muscle PM without perforating visceral pericardium VP. It should be noted that alternate suitable implant sites for embodiments of fixation member tines described herein can be along any endocardial surface defined by pectinate muscle PM.

Figure 3A:
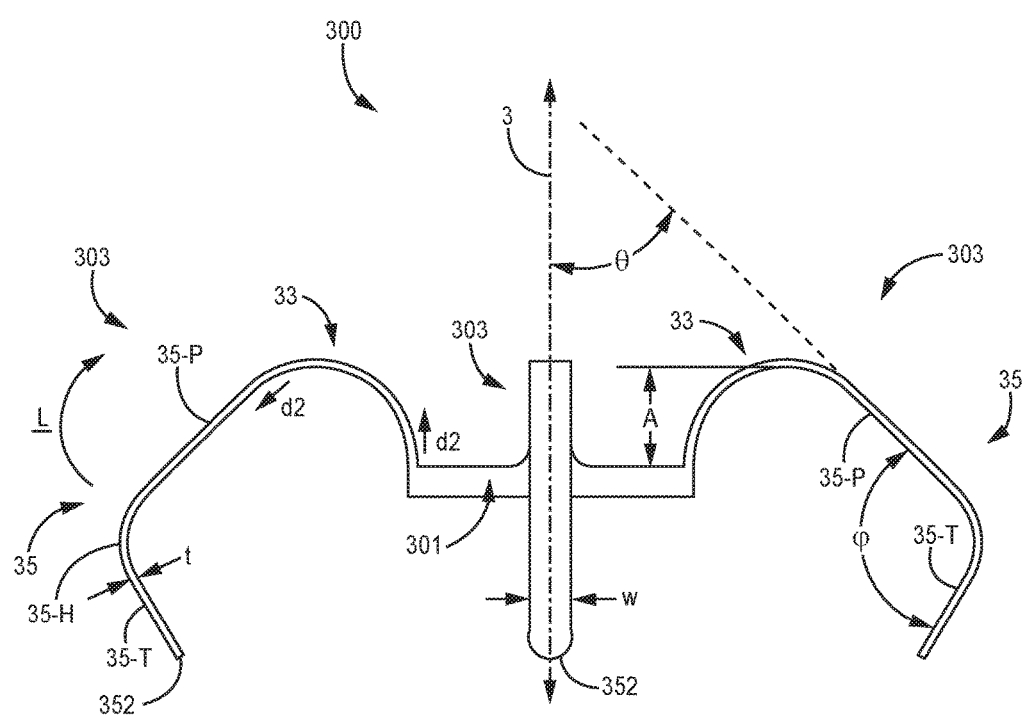
FIG. 3A is an elevation view of an exemplary fixation component which may be employed by the device of FIG. 2A, according to some embodiments.
Figure 3B:
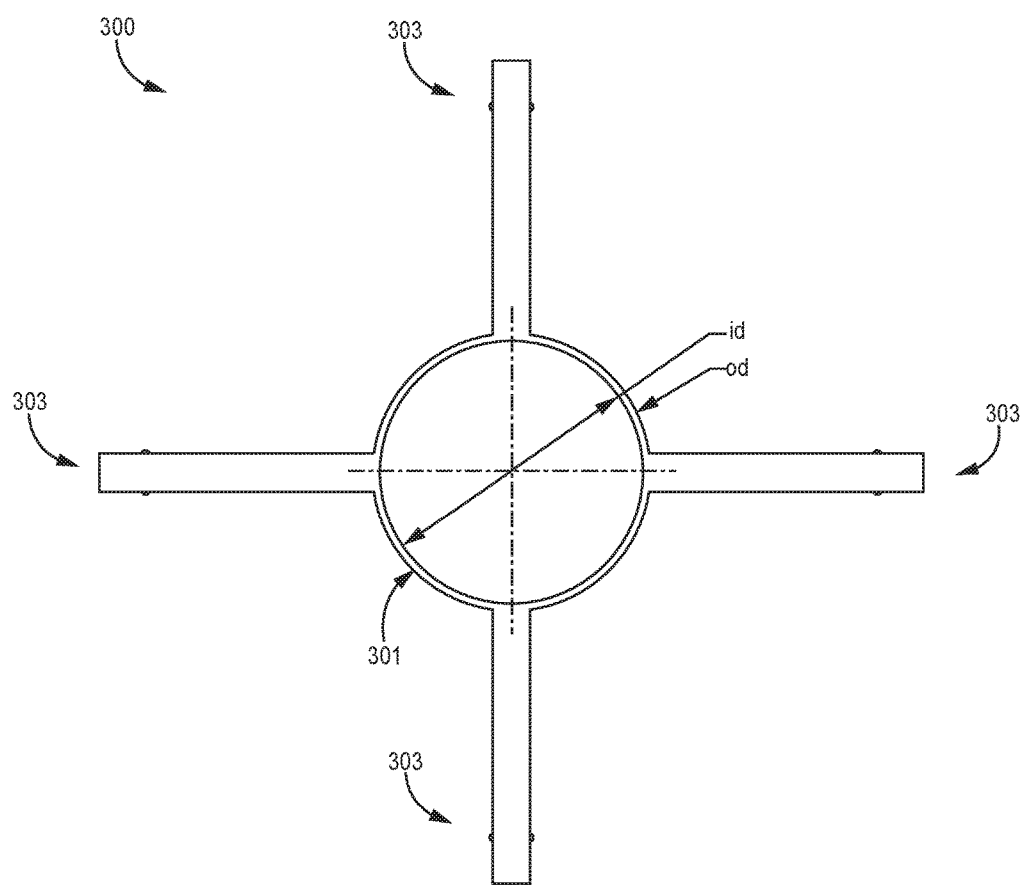
FIG. 3B is an end view of the component of FIG. 3A, according to some embodiments.

FIGS. 3A-B are elevation and end views of a fixation component 300 that forms fixation mechanism 30, according to some embodiments. FIGS. 3A-B illustrate component 300 including a base 301 from which a plurality of tines 303 extend, being spaced apart from one another around a perimeter of base 301. Tines 303 are shown in a relaxed, or pre-formed spring-biased condition. In FIG. 3A, a longitudinal axis 3 of component 300 is shown being defined by base 301 such that, when base 301 is mounted around distal end 202 of device housing 205, and a perimeter of component 300 extends around electrode 206, axis 3 is generally aligned along longitudinal axis 2 of device 20 (FIG. 2A). With reference to FIG. 3B, base 301 may have an inner diameter id of about 0.20 inch and an outer diameter od of about 0.21 inch. Fixation component 300 may be mounted to distal end 202 of device housing 205, for example, in a manner similar to that described for a fixation component 102 in co-pending and commonly assigned United States Patent Application 2012/0172690 (filed on Oct. 28, 2011), which description is hereby incorporated by reference. However, according to some alternate embodiments, fixation mechanism 30 may be separately formed tines 303 (not integrated together with base 301) that are individually mounted to distal end 202 of device housing 205.

Tines 303 are preferably formed from a super-elastic material, for example, a Nickel-Titanium alloy (Nitinol). Fixation component 300 may be cut from a medical grade Nitinol tubing that conforms to the chemical, physical, mechanical, and metallurgical requirements of the ASTM F2063 standard, and has a wall thickness of about 0.005 inch. In this case, tines 303 are integrally formed with base 301 and each tine 303 may have a constant thickness t of 0.005 inch±0.001 inch. After cutting the tubing, tines 303 are shaped into the configuration shown in FIG. 3A by bending and holding tines 303, while heat treating according to methods known to those skilled in the art.

FIG. 3A illustrates each tine 303 including a proximal, spring portion 33, which corresponds to first segment S1 of FIG. 2A, and a distal portion 35, which corresponds to second and third segments S2, S3 of FIG. 2A, and which is terminated by free distal end 352. Free distal end 352 is preferably rounded, as shown in FIG. 3A. FIG. 3A further illustrates distal portion 35 including a proximal section 35-P, a hook section 35-H, and a tip section 35-T. The shaped configuration and width of each tine 303, along with the super-elastic stiffness properties of Nitinol, provide a sufficient spring force and structural stiffness for tines 303 to engage tissue for the fixation of device 20 at an implant site when deployed by delivery tool 400, as described in greater detail below. With reference to FIG. 3A, each tine 303 has a width w which is preferably no less than about 0.02 inch, for example, being in a range from about 0.025 inch to about 0.032 inch. Such a width provides the aforementioned structural stiffness, as well as a radiopaque density that facilitates fluoroscopic visualization during and after the implant procedure.

With further reference to FIG. 3A, according to the illustrated embodiment, each proximal, spring portion 33 is fixedly attached to base 301 and has a spring-biased pre-formed curvature, which, in proximity to the base, extends in a first direction d1, generally parallel to axis 3, and then sweeps laterally, outward from axis 3 to distal portion proximal section 35-P. Distal portion proximal section 35-P, according to the illustrate embodiment, is pre-formed to extend in a second direction d2 and along a relatively straight line (dashed line), being oriented, by the spring-biased pre-formed curvature of proximal, spring portion 33, so that second direction d2 is generally opposite first direction d1, and the relatively straight line intersects axis 3 at an acute angle θ. According to some embodiments, angle θ is between about 30 degrees and about 50 degrees. In an exemplary embodiment of component 300, to be employed by an exemplary embodiment of device 20 that has housing 205 sized to an outer diameter of about 0.26 inch (20 French), the spring-biased pre-formed curvature of each proximal, spring portion 33 is defined by a single radius of 0.067 inch±0.010 inch; a distance A between base 301 and each intersection of proximal, spring portion 33 and distal portion proximal segment 35-P is 0.092 inch±0.005 inch; a length of each distal portion proximal segment 35-P is 0.100 inch±0.005 inch; and angle θ is about 45 degrees.

With further reference to FIG. 3A, each distal portion hook section 35-H has a deformable pre-formed curvature that extends from proximal, spring portion 33 back toward axis 3. FIG. 3A further illustrates tip section 35-T of distal portion 35 extending from hook section 35-T along a relatively straight line to rounded free distal end 352. Tip section 35-T is shown oriented by the pre-formed curvature of hook section 35-H, when un-deformed, to extend toward axis 3, such that tip section 35-T and proximal section 35-P are shown enclosing an angle φ, which, according to the illustrated embodiment, is no less than about 90 degrees, but can be up to about 120 degrees. In the aforementioned exemplary embodiment of component 300, the deformable pre-formed curvature of each hook section 35-H, when un-deformed, is defined by a single radius of about 0.05 inch; and a length of each tip section 35-T is 0.064 inch±0.005 inch.

FIGS. 3C-D are plan views of alternate tine embodiments prior to being formed into the configuration of FIG. 3A, wherein tine 303-105' of FIG. 3C is suitable for an exemplary component 300 in which angle φ is about 105 degrees, and wherein tine 303-90' of FIG. 3D is suitable for an exemplary component 300 in which angle φ is about 90 degrees. With further reference to FIGS. 3C-D, an exemplary width w of each tine 303 is 0.028 inch±0.001 inch, and, in the tine embodiment of FIG. 3C, rounded free distal end 352 of tine 303-105° has an enlarged width defined by a diameter of 0.030 inch±0.001 inch.

Figure 4:
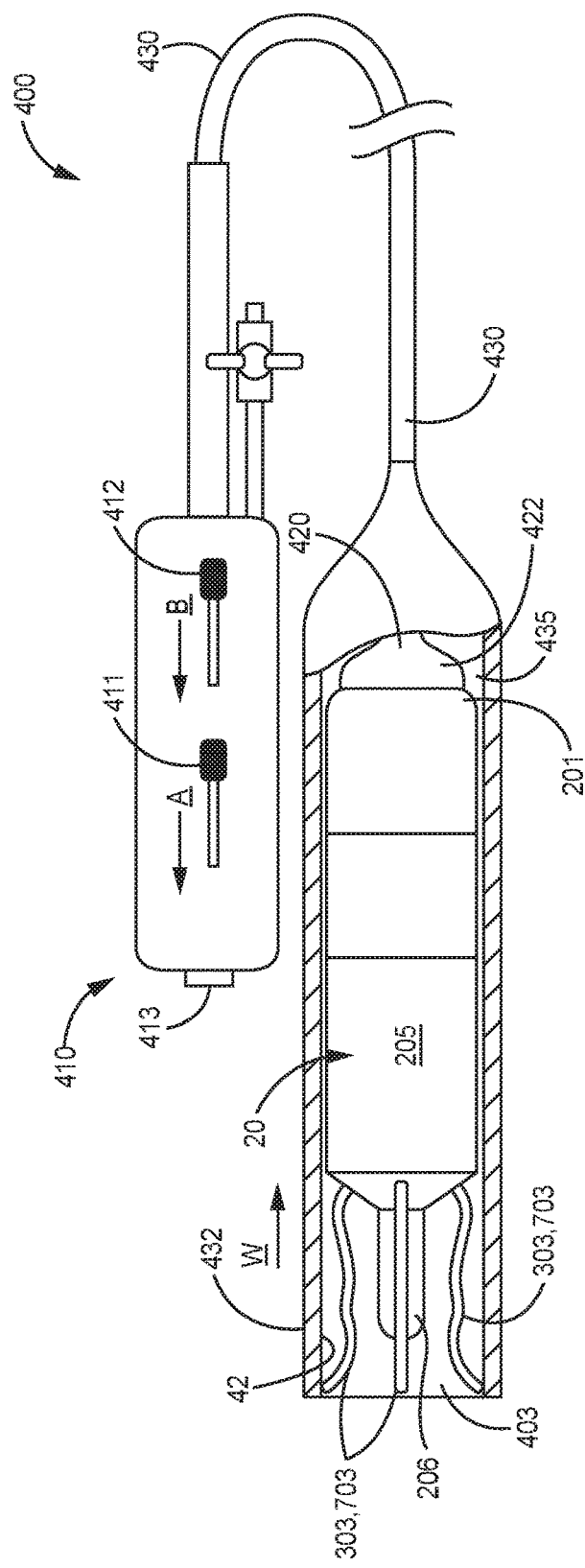
FIG. 4 is a plan view of a medical device system with a partial cut-away section, according to some embodiments.

FIG. 4 is a plan view of medical device system with a partial cut-away section, according to some embodiments, wherein the system includes device 20 and a delivery tool 400, in which device 20 is loaded for deployment to a target implant site. FIG. 4 illustrates tool 400 including a handle 410, an elongate outer member 430, and an elongate inner member 420 that extends within lumen 435 of outer member 430. FIG. 4 further illustrates inner member 420 including a distal end 422, which is configured to engage implantable medical device 20 by abutting proximal end 201 of device housing 205, as shown in the cut-away section. An entirety of device 20 is shown loaded within a tubular sidewall 432 that defines a distal portion of outer member lumen 435, for example, having been loaded therein by pulling device 20, with housing proximal end 201 leading, in through lumen distal opening 403. According to the illustrated embodiment, an inner surface 42 of tubular sidewall 432 engages tines 303 (or 703 as described below in conjunction with FIG. 6A), as device 20 is loaded into lumen 435, to deform tines 303, per arrow L of FIG. 3A, and then to hold each tine 303 of the loaded device 20 in a spring-loaded condition, which is described below in conjunction with FIG. 5A. According to the above-described exemplary embodiments of fixation component 300, with device housing 205 sized to an outer diameter of about 0.26 inch (20 French), a diameter of lumen 435, defined by inner surface 42, is about 0.28 inch (21 French).

With further reference to FIG. 4, a proximal end of outer member 430 is coupled to a control member 412 of handle 410 such that an entirety of outer member 430 is movable with respect to inner member 420, via control member 412, for example, so that an operator may retract outer member 430, per arrow W, relative to device 20 and inner member 420, to deploy device 20 out through distal opening 403, after positioning the system in proximity to a target implant site. The operator may position the system by advancing tool 400 through a venous system of the patient, for example, from a femoral venous access site and up through the inferior vena cava IVC (FIG. 1). Delivery tool 400 may include articulating features to facilitate the navigation of the distal portion of delivery tool 400. For example, inner member 420 of delivery tool 400 may include a pull wire assembly (not shown) integrated therein and being coupled to another control member 411 of handle 410 that, when moved per arrow A, causes inner member 420 and outer member 430 to bend along distal portions thereof. A length of outer member 430, between handle 410 and distal opening 403, when outer member 430 is in the position shown in FIG. 4, may be between about 103 cm and about 107 cm, for example, to reach into the right atrium RA from the femoral access site. Suitable construction detail for a delivery tool like tool 400 is described in co-pending and commonly assigned U.S. Patent Application 2015/0094668, Ser. No. 14/039,937 (Atty. Docket No. C00005393.USU1; filed on Sep. 27, 2013), the description of which is hereby incorporated by reference.

According to some methods, once the operator has advanced the system of FIG. 4 into atrial appendage 102 (FIG. 1), so that distal opening 403 abuts pectinate muscle PM therein (FIG. 2B) at the target implant site, the operator can move control member 412, per arrow B, to retract outer member 430 relative to device 20 and thereby release the spring loading of fixation component 300 so that tines 303 engage with pectinate muscle PM to secure device 20 at the implant site, as illustrated in FIG. 2B. However, it should be noted that, according to alternative embodiments and methods, delivery tool 400 may be configured so that an operator can advance inner member 420 relative to outer member 430 to push device 20 out through distal opening 403 for deployment. FIGS. 5A-F are schematics outlining a sequence of events corresponding to the release of above-described embodiments of fixation tines 303. (Although the schematics show tines 303 integrally formed with base 301, as in above-described embodiments of component 300, it should be understood that the sequence of events in FIGS. 5A-F may also apply to alternate embodiments in which tines 303 are not integrally formed with base 301.) FIG. 5A illustrates a maximum deformation of tines 303 when held in the spring-loaded condition by the engagement of rounded free distal end 352 with inner surface 42 of outer member tubular sidewall 432, wherein proximal, spring portion 33 becomes relatively straightened, and a location of the maximum principle strain along each tine 303 is in relatively close proximity to base 301 (designated by dashed-line circle). With reference back to FIG. 3A, the aforementioned exemplary length of distal portion tip section 35-T and the aforementioned associated angle φ (no less than 90 degrees) help to keep the deformed tines 303 from touching one another within lumen 435 and to prevent free distal ends 352 from being pulled proximally, per arrow P, when outer member 430 is retracted to release the spring loading of tines 303. FIG. 5A further illustrates tip section 35-T extending away from axis 3 at an acute angle δ, which is preferably in a range from about 45 degrees to about 75 degrees for an initial release of the spring loading of each tine 303, upon retraction of outer member 430, as depicted in FIG. 5B. With reference to FIG. 5C, once free distal end 352 is released from engagement with inner surface 42 for deployment into tissue at the implant site, the spring force of proximal, spring portion 33 and the pre-formed curvature of distal portion hook section 35-T cause distal portion tip section 35-T to immediately rotate away from axis 3 to an angle π, which approaches 90 degrees, so that tip section 35-T is oriented approximately normal to axis 3 for initial penetration of pectinate muscle PM. Thus each tine free distal end 352 is deployed in a direction toward pectinate muscle PM that ultimately prevents tines 303 from perforating the underlying visceral pericardium VP (reference FIG. 2B). FIGS. 5D-F illustrates the subsequent movement of tines 303, being driven by the release of proximal, spring portion 33 from the spring loading. According to the illustrated embodiment, this release of proximal, spring portion 33 causes free distal end 352, after penetrating through pectinate muscle PM in a first direction, at a first location P1, to penetrate back through in an opposite direction, at a second location P2, so that device 20 may be securely fixed at the implant site, as illustrated in FIG. 2B.

The configuration of tine distal portion 35, for example, embodied by the aforementioned exemplary lengths of proximal section 35-P and tip section 35-T, and the pre-formed curvature of hook section 35-H, provide a structural stiffness and reach to each tine 303 that is sufficient for deformation and subsequent penetration of free distal end 352 through pectinate muscle PM, as shown in FIG. 2B, but is not sufficient for penetration through visceral pericardium VP. Even if the operator ends up advancing the system into appendage 102 so that distal opening 403 of tool 400 abuts visceral pericardium VP, between folds of pectinate muscle PM, free distal end 352, according to this configuration of tines 303, is not backed-up by sufficient stiffness to penetrate through visceral pericardium VP, so tip section 35-T of tine distal portion 35 is redirected, laterally, toward pectinate muscle PM.

It should be noted that an operator may employ tines 303 to secure device 20 in atrial appendage 102 in an alternative fashion, wherein tines 303 are fully released from the spring-loaded condition without engaging any tissue (FIG. 5F), and then device 20 is advanced to the implant site so that tines 303 wedge between opposing surfaces of pectinate muscle PM within atrial appendage 102 to secure device 20 in place.

With reference back to FIGS. 2A-B, according to some preferred embodiments, for example, in order to assure intimate contact of electrode 206 with tissue, when fixation tines 303 secure device 20 at a target implant site, electrode 206 is spaced distally apart from device housing distal end 202 by a distance along longitudinal axis 2. Electrode 206 may be approximately flush with an intersection between proximal, spring portion 33 and distal portion 35, or spaced distally apart from the intersection by a distance X that may be up to about 2 mm, as depicted in FIG. 2A.

Figure 6A:
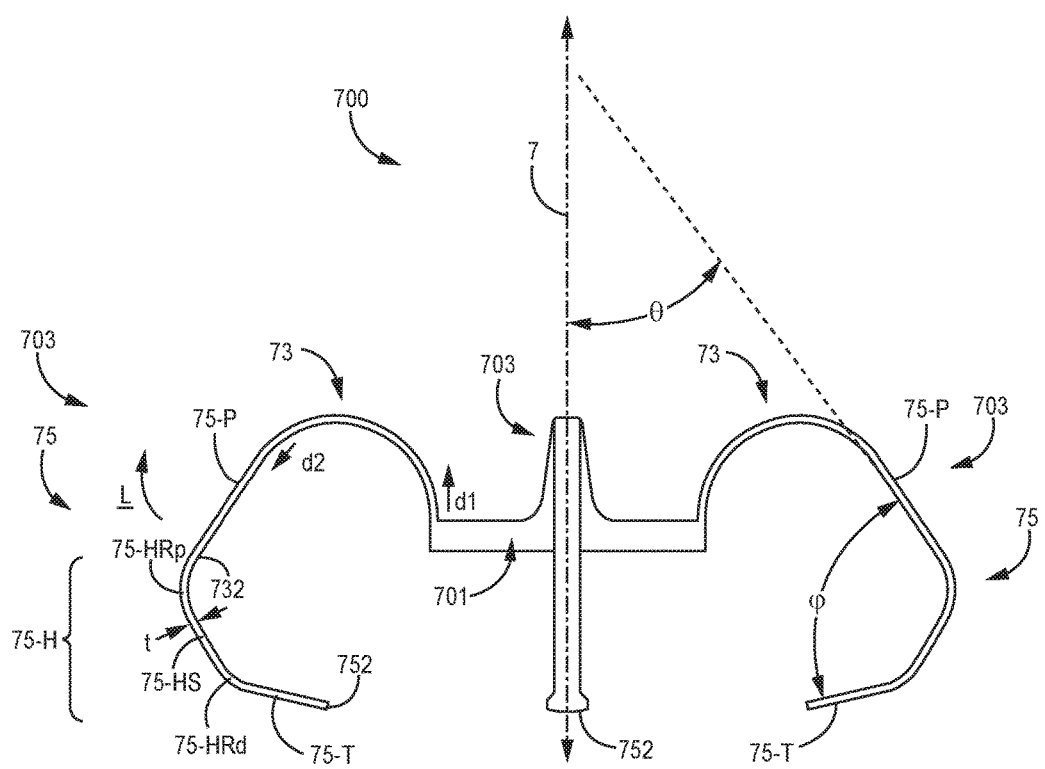
FIG. 6A is an elevation view of an exemplary fixation component which may be employed by the device of FIG. 2A, according to some additional embodiments.
Figure 6B:
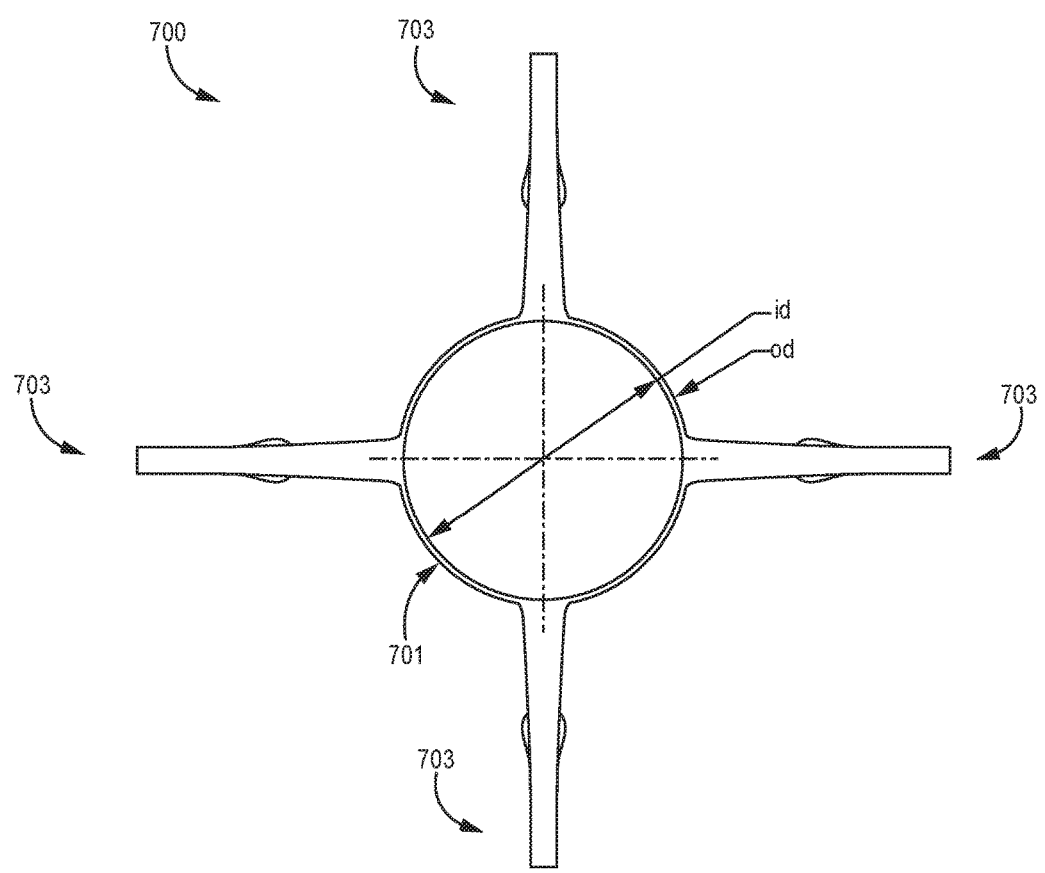
FIG. 6B is an end view of the component of FIG. 6A, according to some additional embodiments.

FIG. 6A-B are elevation and end views of an exemplary fixation component 700 which may be employed by device 20, according to some additional embodiments. FIGS. 6A-B illustrate component 700 including a base 701 from which a plurality of tines 703 extend, being spaced apart from one another around a perimeter of base 701. In FIG. 6A, a longitudinal axis 7 of component 700 is shown being defined by base 701 such that, when base 701 is mounted around distal end 202 of device housing 205, so that a perimeter of component 700 extends around electrode 206, axis 7 is generally aligned along longitudinal axis 2 of device 20

(FIG. 2A). With reference to FIG. 6B, base 701 may have an inner diameter id of about 0.20 inch and an outer diameter od of about 0.21 inch.

Like component 300, component 700 may be cut from the aforementioned medical grade Nitinol tubing, and each tine 703, integrally formed with base 701, may have a constant thickness t of 0.005 inch±0.001 inch. After cutting the tubing, tines 703 are shaped into the configuration shown in FIG. 6A by bending and holding tines 703, while heat treating according to methods known to those skilled in the art. FIG. 6A illustrates each tine 703 including a proximal, spring portion 73 and distal portion 75, which is terminated by a rounded free distal end 752, wherein both portions 73, 75 are pre-formed into, and elastically deformable from the illustrated shape. The shaped configuration and width of each tine 703, along with the super-elastic stiffness properties of Nitinol, provide a sufficient spring force and structural stiffness for tines 703 to engage tissue for the fixation of device 20 at an implant site when deployed by delivery tool 400, as described above for component 300. Furthermore, each tine 703, when device 20 is loaded in delivery tool 400, becomes deformed as generally shown in FIG. 4.

According to the illustrated embodiment, each proximal, spring portion 73 is fixedly attached to base 701 and has a spring-biased pre-formed curvature, which, in proximity to the base, extends in a first direction d1, generally parallel to axis 7, and then sweeps laterally, outward from axis 7 to a proximal section 73-P of distal portion 75. Proximal section 73-P is shown pre-formed to extend in a second direction d2 and along a relatively straight line (dashed line), being oriented, by the spring-biased pre-formed curvature of proximal, spring portion 73, so that second direction d2 is generally opposite first direction d1, and the relatively straight line intersects axis 7 at acute angle θ, which, according to some embodiments, is between about 30 degrees and about 50 degrees. In an exemplary embodiment of component 700, to be employed by an exemplary embodiment of device 20 that has housing 205 sized to an outer diameter of about 0.26 inch (20 French), the spring-biased pre-formed curvature of each proximal, spring portion 73 is defined by a single radius of 0.067 inch ±0.010 inch; a distance A between base 701 and each intersection of proximal, spring portion 73 and distal portion proximal segment 75-P is 0.092 inch ±0.005 inch; a length of each spring segment distal segment 73-D is 0.085 inch ±0.005 inch; and angle θ is about 34 degrees.

With further reference to FIG. 6A, each distal portion 75 further includes a hook section 75-H, which has a deformable pre-formed curvature extending from distal proximal, spring portion 73 back toward axis 7, and a tip section 75-T, which is pre-formed to extend along a relatively straight line. Tip section 75-T is shown oriented, by un-deformed hook segment 74, to extend toward axis 7, such that tip section 75-T and proximal section 75-D enclose an angle φ, which may be about 70 degrees. According to the illustrated embodiment, distal portion hook section 75-H is defined by proximal and distal radii 75-HRp, 75-HRd, and a straight length 75-HS that extends therebetween. In the aforementioned exemplary embodiment of component 700, each hook section proximal radius 75-HRp, when un-deformed, is about 0.040 inch, each hook section distal radius 75-HRd is about 0.030 inch, and each straight length 75-HS is about 0.040 inch; and a length of each tip section 75-T is 0.062 inch ±0.005 inch. It is contemplated that this double radius configuration of distal portion hook sections 75-H of component 700 enhances a stability of fixation for device 20 over that of component 300, by a decreased stiffness of tines 703 in proximity to free distal end 752 and additional spring energy to draw each tine 703 further away from the aforementioned second location P2 of penetration through pectinate muscle PM (FIG. 2B).

Figure 6C:
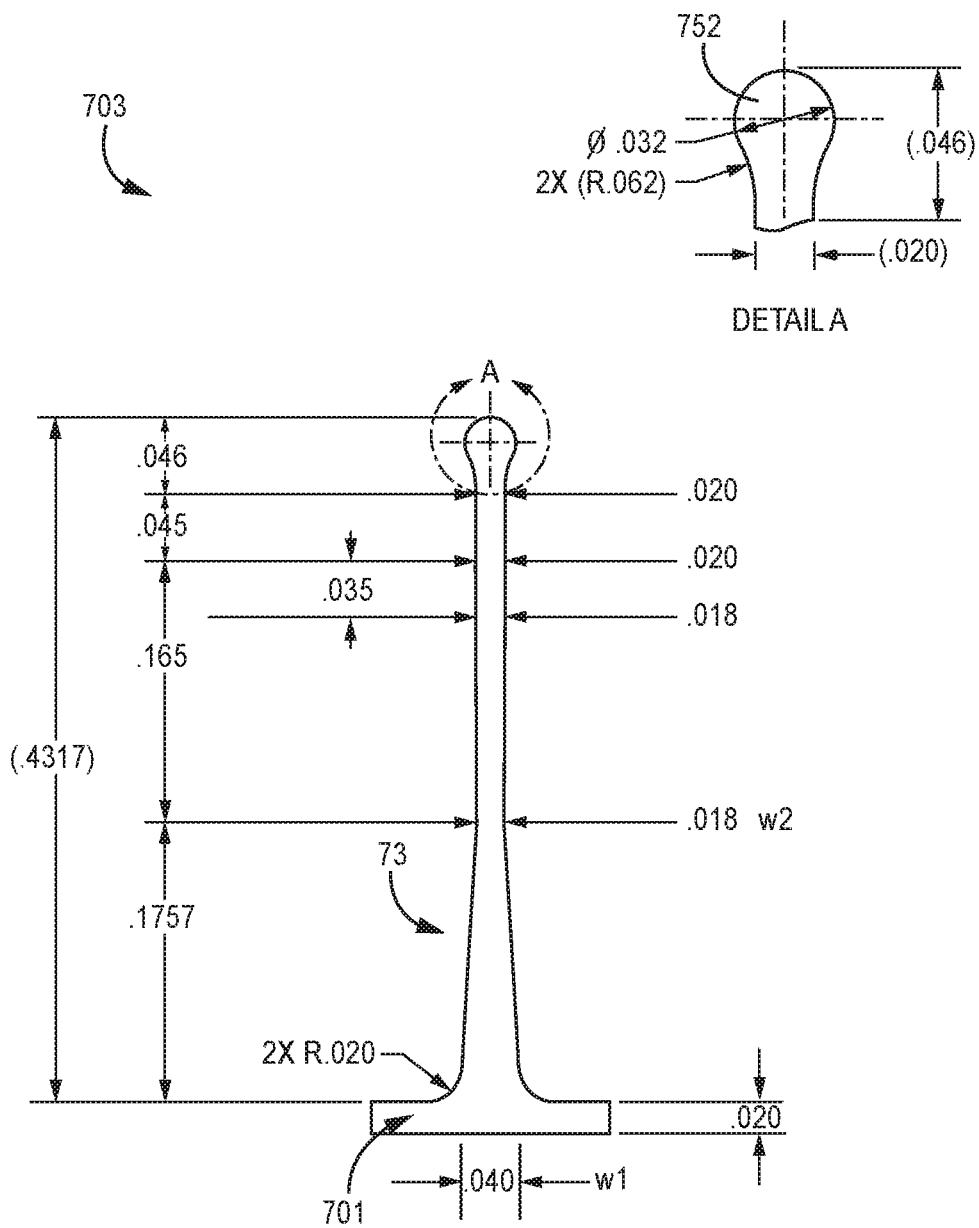
FIG. 6C is a plan view of a portion of the component of FIGS. 6A-B, prior to forming, according to some embodiments.
Figure 6D:
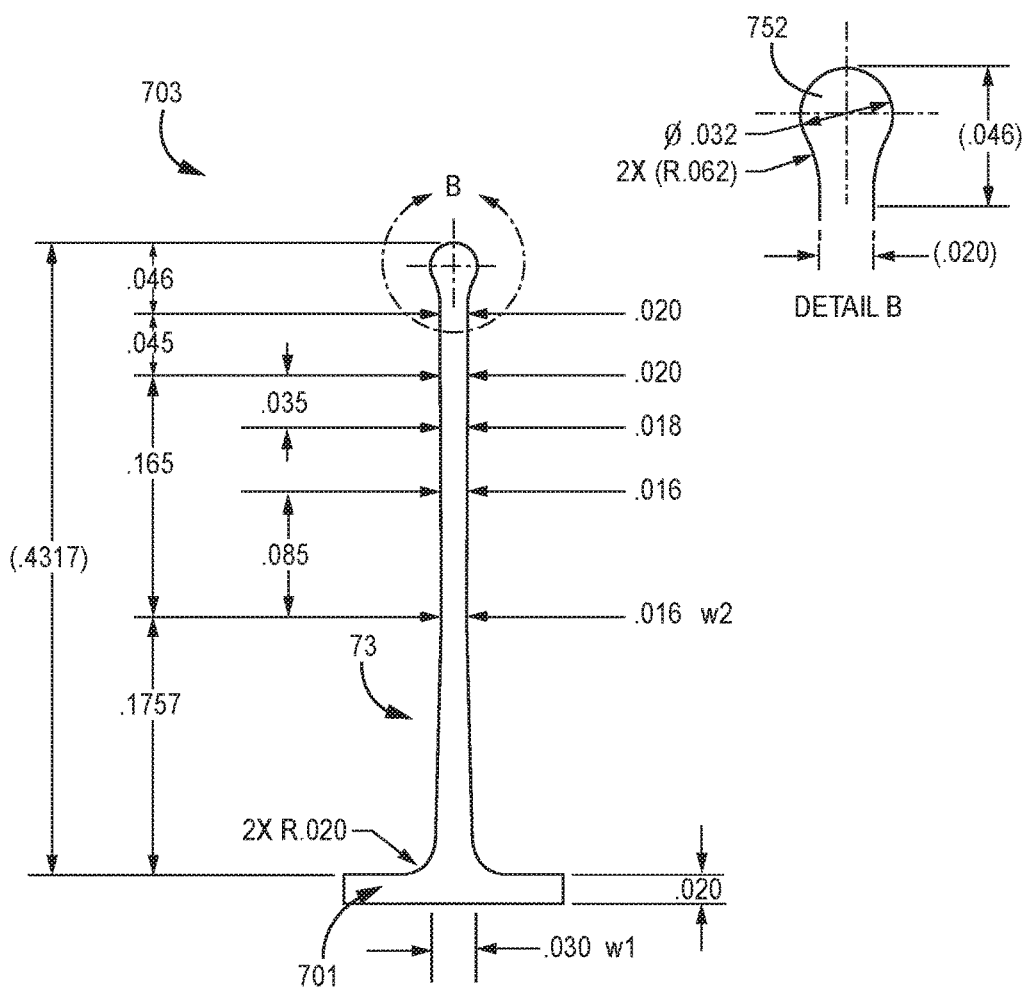
FIG. 6D is a plan view of a portion of the component of FIGS. 6A-B, prior to forming, according to some alternate embodiments.

FIGS. 6C-D are plan views of alternate embodiments of each tine 703, prior to being formed into the configuration of FIG. 6A, wherein exemplary dimensions, in inches, for the alternate embodiments are shown. FIGS. 6C-D illustrate rounded free distal end 752 of each tine 703 having an enlarged width, for example, defined by a diameter of 0.032 inch ±0.001 inch. FIG. 6C-D further illustrate a tapering width along a length of each tine 703, wherein proximal, spring portion 73 tapers from a first width w1 in proximity to base to a smaller second width w2. The tapering width may be employed to tailor spring energy and stiffness of tines, for example, to prevent tissue erosion and to enhance the fatigue life of tines 703 over the term of an implant.

In the foregoing detailed description, specific exemplary embodiments have been described. However, it may be appreciated that various modifications and changes can be made without departing from the scope of the invention as set forth in the appended claims.

We claim:

1. A tissue penetrating fixation component for an implantable medical device, the component comprising a base and a plurality of tines, the base defining a longitudinal axis of the component and being configured to be fixedly attached to the device so that a perimeter of the component extends around an electrode of the device, and so that the longitudinal axis of the component is generally aligned along a longitudinal axis of the device, the plurality of tines extending from the base and being spaced apart from one another around a perimeter thereof, and each tine comprising:

a proximal, spring portion being fixedly attached to the base and having a spring-biased pre-formed curvature, the pre-formed curvature, in proximity to the base, extending in a first direction, generally parallel to the axis of the component, and then sweeping laterally, outward from the axis; and a distal portion including a proximal section, a hook section, and tip section terminated by a rounded free distal end, the proximal section extending from the proximal, spring portion and being pre-formed to extend in a second direction and along a relatively straight line to the hook section, the proximal section being oriented, by the spring-biased pre-formed curvature of the proximal, spring portion, so that the second direction is generally opposite the first direction, and the relatively straight line intersects the axis at an acute angle of between about 30 degrees and about 50 degrees, the hook section having a deformable preformed curvature that extends from the proximal section back toward the axis of the component, the tip section being pre-formed to extend along a relatively straight line from the hook section to the rounded free distal end, and the tip section being oriented by the pre-formed curvature of the hook section, when undeformed, to extend toward the axis of the component, such that the tip section and the proximal section enclose an angle in a range from about 70 degrees to about 120 degrees; and wherein, when the device, having the fixation component fixedly attached thereto, is loaded within a tubular sidewall of a delivery tool, so that the rounded free distal end of each tine of the component engages an inner surface of the sidewall in proximity to a distal opening of the tool, to hold the proximal, spring portion of each tine of the component in a spring-loaded condition, each tip section of the distal portion extends away from the axis of the component at an acute angle in a range from about 45 degrees to about 75 degrees for deployment of the corresponding rounded free distal end out from the distal opening of the tool tubular sidewall; and upon deployment of the rounded free distal end of each tine, the tip section of each distal portion rotates away from the axis to approach an angle of 90 degrees, relative to the axis, in response to an initial release of the spring-loaded condition of the corresponding proximal, spring portion.

2. The component of claim 1, wherein each tine has a constant thickness of about 0.005 inch and a width no less than about 0.02 inch.

3. The component of claim 2, wherein the width of each tine tapers from a greater width in proximity to the base to a lesser width in proximity to the hook section of the distal portion.

4. The component of claim 3, wherein the rounded free distal end of each tine has an enlarged width relative to a remainder of the tip section of the corresponding distal portion.

5. The component of claim 1, wherein the spring-biased pre-formed curvature of the proximal, spring portion of each tine is defined by a single radius, the radius being between about 0.06 inch and about 0.08 inch.

6. The component of claim 1, wherein the tip section of the distal portion of each tine has a length of about 0.06 inch.

7. The component of claim 1, wherein the proximal section of the distal portion of each tine has a length of about 0.1 inch.

8. The component of claim 1, wherein the deformable pre-formed curvature of the hook section of the distal portion of each tine is defined by a single radius, when un-deformed, the radius being about 0.05 inch.

9. The component of claim 1, wherein the acute angle of the relatively straight line of the proximal section of the distal portion of each tine is about 45 degrees.

10. The component of claim 1, wherein the deformable pre-formed curvature of the hook section of the distal portion of each tine, when un-deformed, orients the corresponding tip section to enclose, with the corresponding proximal section, an angle of no less than about 90 degrees.

11. The component of claim 1, wherein:

the deformable pre-formed curvature of the hook section of the distal portion of each tine, when un-deformed, is defined by two radii and a straight length extending therebetween, the straight length being about 0.04 inch; and the proximal section of the distal portion of each tine has a length of about 0.085 inch.

12. An implantable medical device having a longitudinal axis and including a housing, an electrode, and a fixation mechanism, the housing having a proximal end and a distal end, between which the longitudinal axis extends, the electrode being mounted in proximity to the housing distal end, and the fixation mechanism comprising a plurality of tines formed from an elastically deformable material, the tines being fixedly mounted and spaced from one another around a perimeter of the housing distal end, and wherein each tine of the fixation mechanism comprises:

a proximal, spring portion being fixedly attached to the device housing and having a spring-biased pre-formed curvature, the pre-formed curvature, in proximity to the housing, extending in a first direction, generally parallel to the axis of the device, and then sweeping laterally, outward from the axis; and a distal portion including a proximal section, a hook section, and tip section terminated by a rounded free distal end, the proximal section extending from the proximal, spring portion and being pre-formed to extend in a second direction and along a relatively straight line to the hook section, the proximal section being oriented, by the spring-biased pre-formed curvature of the proximal, spring portion, so that the second direction is generally opposite the first direction, and the relatively straight line intersects the axis of the device at an acute angle of between about 30 degrees and about 50 degrees, the hook section having a deformable pre-formed curvature that extends from the proximal section back toward the axis of the device, the tip section being pre-formed to extend along a relatively straight line from the hook section to the rounded free distal end, and the tip section being oriented by the pre-formed curvature of the hook section, when un-deformed, to extend toward the axis of the device, such that the tip section and the proximal section enclose an angle in a range from about 70 degrees to about 120 degrees; and wherein, when the device is loaded within a tubular sidewall of a delivery tool, so that the rounded free distal end of each tine of the fixation mechanism engages an inner surface of the sidewall in proximity to a distal opening of the tool, to hold the proximal, spring portion of each tine in a spring-loaded condition, each tip section of the distal portion extends away from the axis of the component at an acute angle in a range from about 45 degrees to about 75 degrees for deployment of the corresponding rounded free distal end out from the distal opening of the tool tubular sidewall; and upon deployment of the rounded free distal end of each tine, the tip section of each distal portion rotates away from the axis to approach an angle of 90 degrees, relative to the axis, in response to an initial release of the spring-loaded condition of the corresponding proximal, spring portion.

13. The device of claim 12, wherein each tine of the fixation mechanism has a constant thickness of about 0.005 inch and a width no less than about 0.02 inch, and the width of each tine tapers from a greater width in proximity to the device housing, where the tine is fixedly attached, to a lesser width in proximity to the hook section of the distal portion.

14. The device of claim 13, wherein the rounded free distal end of each tine of the fixation mechanism has an enlarged width relative to a remainder of the tip section of the corresponding distal portion.

15. The device of claim 12, wherein the spring-biased pre-formed curvature of the proximal, spring portion of each tine of the fixation mechanism is defined by a single radius, the radius being between about 0.06 inch and about 0.08 inch.

16. The device of claim 12, wherein the tip section of the distal portion of each tine of the fixation mechanism has a length of about 0.06 inch.

17. The device of claim 12, wherein the proximal section of the distal portion of each tine of the fixation mechanism has a length of about 0.1 inch.

18. The device of claim 12, wherein the deformable pre-formed curvature of the hook section of the distal portion of each tine of the fixation mechanism is defined by a single radius, when un-deformed, the radius being about 0.05 inch.

19. The device of claim 12, wherein the acute angle of the relatively straight line of the proximal section of the distal portion of each tine of the fixation mechanism is about 45 degrees.

20. The device of claim 12, wherein the deformable pre-formed curvature of the hook section of the distal portion of each tine of the fixation mechanism, when un-deformed, orients the corresponding tip section to enclose, with the corresponding proximal section, an angle of no less than about 90 degrees.

21. The device of claim 12, wherein:
the deformable pre-formed curvature of the hook section of the distal portion of each tine of the fixation mechanism, when un-deformed, is defined by two radii and a straight length extending therebetween, the straight length being about 0.04 inch; and
the proximal section of the distal portion of each tine of the fixation mechanism has a length of about 0.085 inch.

22. The device of claim 12, wherein:
an intersection between the proximal, spring portion and the distal portion of each tine of the fixation mechanism is spaced distally from the housing distal end; and
the electrode is flush with, or spaced distally apart from the intersection between the proximal, spring portion and the distal portion of each tine by a distance in a range from about 0 mm to about 2 mm.

23. An implantable medical device having a longitudinal axis and including a housing, an electrode, and a fixation mechanism, the housing having a proximal end and a distal end, between which the longitudinal axis extends, the electrode being mounted in proximity to the housing distal end, and the fixation mechanism comprising a plurality of tines formed from an elastically deformable material, the tines being fixedly mounted and spaced from one another around a perimeter of the housing distal end, and wherein each tine of the fixation mechanism comprises:
a first segment fixedly attached to the device housing and extending therefrom;
a second segment extending from the first segment; and
a third segment, to which the second segment extends, the third segment having a rounded free distal end spaced from the perimeter of the device housing distal end; and
wherein the first segment has a spring-biased pre-formed curvature, the pre-formed curvature extending distally from the device housing distal end, and then sweeping laterally outward from the axis of the device and then proximally to the second segment;
the second segment is pre-formed to extend proximally along a relatively straight line to the third segment, the relatively straight line of the second segment being oriented, by the spring-biased preformed curvature of the first segment, to intersect the axis of the device at an acute angle of between about 30 degrees and about 50 degrees; and
the third segment has a deformable pre-formed curvature that extends back toward the axis of the device, such that, when the curvature of the third segment is un-deformed, the second and third segments enclose an angle in a range from about 70 degrees to about 120 degrees.

24. The device of claim 23, wherein the acute angle of the relatively straight line of the second segment of each tine of the fixation mechanism is about 45 degrees.

25. The device of claim 23, wherein the second and third segments of each tine of the fixation mechanism enclose an angle of no less than about 90 degrees, when the corresponding third segment is un-deformed.

26. The device of claim 23, wherein:
an intersection between the first segment and the second segment of each tine of the fixation mechanism is spaced distally from the housing distal end; and
the electrode is flush with, or spaced distally apart from the intersection between the first segment and the second segment of each tine by a distance in a range from about 0 mm to about 2 mm.

27. A medical device system comprising an implantable medical device and a delivery tool, the device having a proximal end, a distal end and a longitudinal axis extending between the proximal and distal ends, the delivery tool including a tubular sidewall that defines a lumen into which the device may be loaded, the lumen having a distal opening through which the device may be deployed; and the device further comprising:
an electrode mounted in proximity to the distal end;
a fixation mechanism comprising a plurality of tines formed from an elastically deformable material, the tines being fixedly mounted and spaced from one another around a perimeter of the device distal end, and each tine comprising:
a first segment fixedly attached to the device and extending therefrom;
a second segment extending from the first segment; and
a third segment, to which the second segment extends, having a rounded free distal end spaced from the perimeter of the device distal end; and
wherein the first segment has a spring-biased pre-formed curvature, extending distally from the device distal end, and then sweeping laterally outward from the axis of the device and then proximally to the second segment;
the second segment is pre-formed to extend proximally along a relatively straight line to the third segment, the relatively straight line of the second segment being oriented, by the spring-biased preformed curvature of the first segment, to intersect the axis of the device at an acute angle of between about 30 degrees and about 50 degrees;
the third segment has a deformable pre-formed curvature that extends back toward the axis of the device such that, when the curvature of the third segment is un-deformed, the second and third segments enclose an angle in a range from about 70 degrees to about 120 degrees; and
the tines are each configured such that when the device is loaded in the lumen of the tool and the rounded free distal end of the third segment of each tine engages the delivery tool sidewall to hold the tines in a spring-loaded condition, the first segment of each tine becomes relatively straightened, and the third segment of each tine extends away from the axis of the device at an acute angle in a range from about 45 degrees to about 75 degrees.

28. The device system of claim 27, wherein the tines are each configured such that, upon deployment of the third segments thereof, out from the distal opening of the tool, each third segment rotates away from the axis of the device to extend at an angle that approaches 90 degrees relative to the axis.

29. The device system of claim 27, wherein the acute angle of the relatively straight line of the second segment of each tine of the device fixation mechanism is about 45 degrees.

30. The device system of claim 27, wherein the second and third segments of each tine of the device fixation mechanism enclose an angle of no less than about 90 degrees, when the corresponding third segment is un-deformed.

31. The device system of claim 27, wherein:
- an intersection between the first segment and the second segment of each tine of the device fixation mechanism is spaced distally from the housing distal end; and
- the electrode is flush with, or spaced distally apart from the intersection between the first segment and the second segment of each tine by a distance in a range from about 0 mm to about 2 mm.

* * * * *